(12) United States Patent
Lee et al.

(10) Patent No.: US 8,361,060 B2
(45) Date of Patent: Jan. 29, 2013

(54) ELECTROMAGNETIC THERMOTHERAPEUTIC APPARATUS AND SYSTEM

(75) Inventors: Gwo-Bin Lee, Tainan (TW); Xi-Zhang Lin, Tainan (TW); Sheng-Chieh Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 595 days.

(21) Appl. No.: 12/573,665

(22) Filed: Oct. 5, 2009

(65) Prior Publication Data

US 2010/0249770 A1 Sep. 30, 2010

(30) Foreign Application Priority Data

Mar. 27, 2009 (TW) ................................ 98110190 A

(51) Int. Cl.
*A61B 18/04* (2006.01)
(52) U.S. Cl. .............................. 606/28; 606/27; 607/103
(58) Field of Classification Search .................. 607/103; 606/33, 41, 44, 27, 28; 600/10, 12
See application file for complete search history.

(56) References Cited

U.S. PATENT DOCUMENTS

| | | | | |
|---|---|---|---|---|
| 6,113,620 | A | * | 9/2000 | Chung ........................... 606/189 |
| 6,423,056 | B1 | * | 7/2002 | Ishikawa et al. ................ 606/28 |
| 7,297,143 | B2 | * | 11/2007 | Woloszko et al. .............. 606/41 |
| 8,140,169 | B2 | * | 3/2012 | Gellman et al. ............... 607/103 |
| 2008/0045879 | A1 | * | 2/2008 | Prausnitz et al. ............... 604/20 |
| 2010/0152763 | A1 | * | 6/2010 | Kim et al. ...................... 606/189 |
| 2011/0258781 | A1 | * | 10/2011 | Kawasaki et al. .............. 5/652.1 |

* cited by examiner

*Primary Examiner* — Linda Dvorak
*Assistant Examiner* — Jocelyn D Ram
(74) *Attorney, Agent, or Firm* — Alan Kamrath; Kamrath IP Lawfirm, P.A.

(57) ABSTRACT

An electromagnetic thermotherapeutic system is adapted to treat a biological tissue and includes an electromagnetic thermotherapeutic apparatus and a high frequency induction heating circuit unit. The apparatus includes a needle assembly and a temperature monitor. The needle assembly is adapted to be inserted in the biological tissue and includes a flexible and bendable needle seat and a plurality of ferrous needles attached to the needle seat and having needle tips extending in a direction away from the needle seat. The temperature monitor is connected to the needle assembly. The high frequency induction heating circuit unit has an induction coil capable of producing an electromagnetic field to induce currents in the ferrous needles and to thereby heat the ferrous needles.

10 Claims, 3 Drawing Sheets

ELECTROMAGNETIC THERMOTHERAPEUTIC APPARATUS AND SYSTEM

CROSS-REFERENCE TO RELATED APPLICATION

This application claims priority of Taiwanese application no. 098110190, filed on Mar. 27, 2009.

BACKGROUND OF THE INVENTION

1. Field of the Invention

This invention relates to a therapeutic apparatus, more particularly to an electromagnetic thermotherapeutic apparatus and a system thereof.

2. Description of the Related Art

Generally, conventional methods of treating organ swelling and resecting an organ include surgical resection, embolization, radiofrequency ablation, etc. However, the methods are complicated, give rise to many side effects, and are costly.

Surgical resection leads to hemorrhage and consequently increases danger to a patient. Embolization is performed by virtue of a minimally invasive surgery to inject embolic gel particles into a desired branch of arteries of an organ using a catheter. Embolization is able to cause occlusion of the desired branch of the arteries of the organ, thereby resulting in necrosis of a swollen tissue of the organ and avoiding the risk of surgical resection. Nevertheless, embolization is limited by the patients' primary disease. Radiofrequency ablation employs a high temperature to induce coagulative necrosis of a desired tissue. Since equipment for radiofrequency ablation is expensive, radiofrequency ablation is not commonly used due to a high cost thereof.

SUMMARY OF THE INVENTION

Therefore, the object of the present invention is to provide an electromagnetic thermotherapeutic apparatus and a system thereof to overcome the aforesaid drawbacks of the prior art.

According to one aspect of this invention, there is provided an electromagnetic thermotherapeutic system. The system is adapted to treat a biological tissue and includes a needle assembly, a high frequency induction heating circuit unit, and a temperature monitor.

The needle assembly is adapted to be inserted in the biological tissue and includes a flexible and bendable needle seat and a plurality of ferrous needles attached to the needle seat and having needle tips extending in a direction away from the needle seat. The high frequency induction heating circuit unit has an induction coil capable of producing an electromagnetic field to induce currents in the ferrous needles and to thereby heat the ferrous needles. The temperature monitor is connected to the needle assembly.

According to another aspect of this invention, there is provided an electromagnetic thermotherapeutic apparatus. The apparatus can be used to treat a biological tissue, can be used in combination with a high frequency induction heating circuit unit, and includes a needle assembly and a temperature monitor.

The needle assembly is adapted to be inserted in the biological tissue and includes a flexible and bendable needle seat and a plurality of ferrous needles that can be induction heated by the high frequency induction heating circuit unit. The ferrous needles are attached to the needle seat and have needle tips extending in a direction away from the needle seat. The temperature monitor is connected to the needle assembly.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 1:
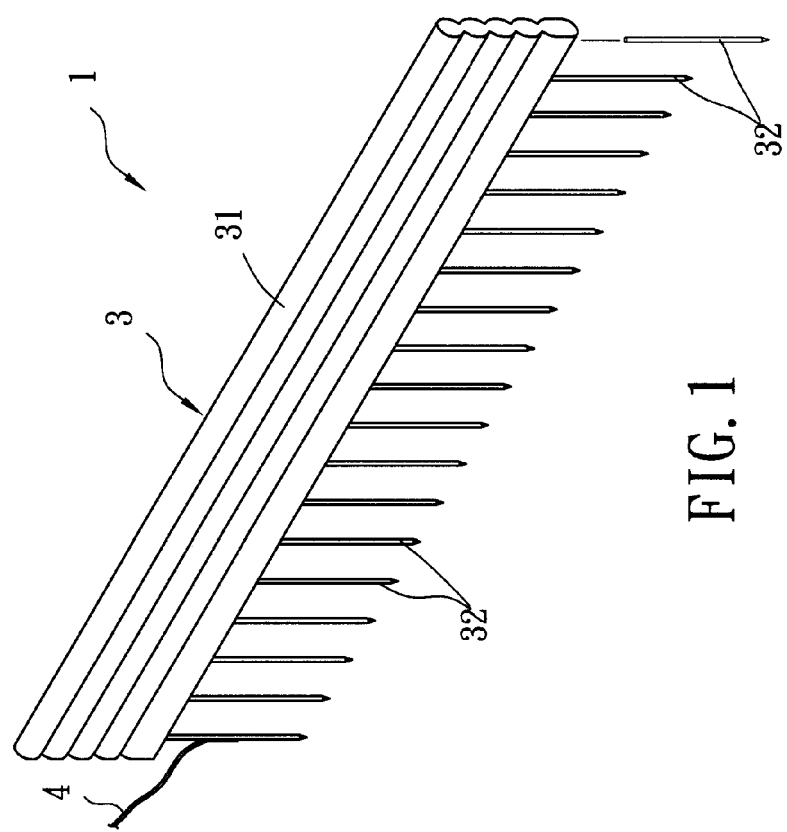
FIG. 1 is a perspective view to illustrate an electromagnetic thermotherapeutic apparatus of an electromagnetic thermotherapeutic system according to this invention.
Figure 2:
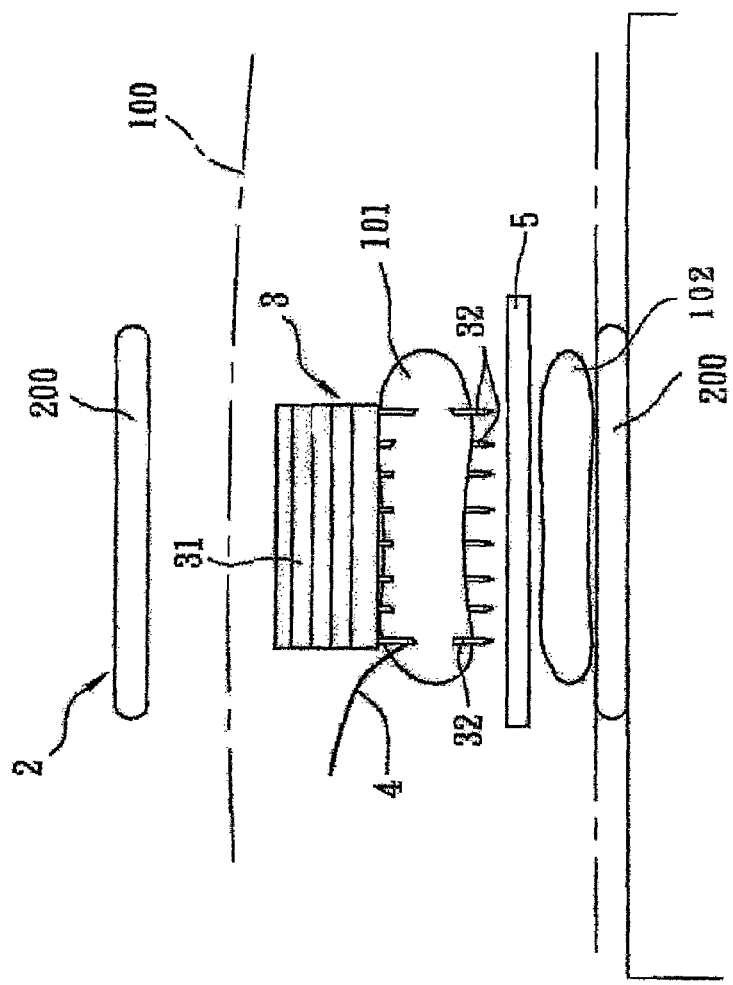
FIG. 2 is a schematic diagram to illustrate the electromagnetic thermotherapeutic system in a state of use.
Figure 3:
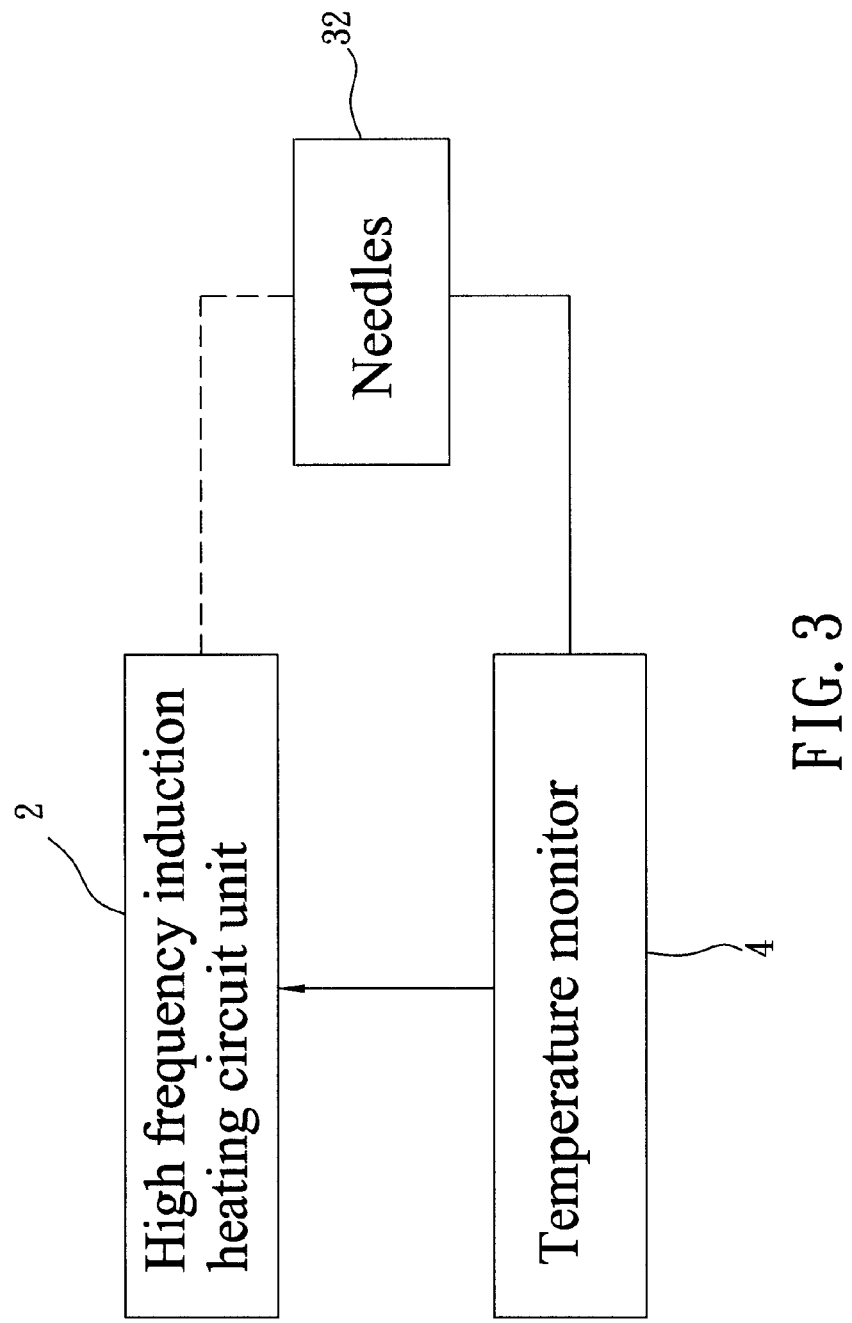
FIG. 3 is a block diagram of the electromagnetic thermotherapeutic system.

Referring to FIGS. 1-3, the preferred embodiment of an electromagnetic thermotherapeutic system according to the present invention includes an electromagnetic thermotherapeutic apparatus 1 and a high frequency induction heating circuit unit 2 and is adapted to treat a biological tissue. For instance, the system can be utilized to heat, cauterize, and destroy a desired biological tissue, or can be applied to heat and cauterize a blood vessel for preventing a massive hemorrhage arising from a surgical operation.

The electromagnetic thermotherapeutic apparatus 1 includes a needle assembly 3 and a temperature monitor 4. The needle assembly 3 is adapted to be inserted in the biological tissue, such as a tissue of an organ 101. The needle assembly 3 includes a flexible and bendable needle seat 31 in the shape of a strip and a plurality of ferrous needles 32 attached to the needle seat 31 and having needle tips extending in a direction away from the needle seat 31. It should be noted that the needle seat 31 could be annular or have another shape in other embodiments.

The needle seat 31 includes a thermochromic material that can change in color in response to a temperature change of the needles 32. In this embodiment, the needle seat is made from a combination that contains the thermochromic material and a flexible polymeric molding material. The needle seat 31 can be bent and deformed into a desired shape. A user is able to identify a temperature change of the needles 32 by virtue of a color change of the needle seat 31. Thus, the color change of the needle seat 31 can be regarded as a warning of overheating the needles 32. Through the use of one kind of the thermochromic material, the needle seat 31 can be designed to change a color thereof when a temperature of the needles 32 is higher than a desired temperature. Alternatively, a multiphase color change of the needle seat 31 can be achieved when different thermochromic materials are mixed together to form the needle seat 31. Therefore, the needle seat 31 is also capable of changing colors thereof in response to different temperature changes of the needles 32.

The flexible polymeric molding material may include a material selected from the group consisting of silicone, rubber, and polydimethylsiloxane. In this embodiment, the flexible polymeric molding material is silicone. The thermochromic material in this embodiment is a product (Model No. 5C2X) of New Prismatic Enterprise Co., Ltd. and is able to perform two-phase color change. Specifically, when the temperature of the needles 32 is higher than 70° C., the needle seat 31 changes from black to white. Consequently, the color change of the needle seat 31 can denote a warning of overheating the needles 32. It should be noted that the needle seat 31 could be designed using different thermochromic materials to perform a two-phase color change, a three-phase color change, or a multi-phase color change within a temperature range of 40° C. to 100° C.

The needles 32 are disposed in an array. In this embodiment, the needles 32 are disposed in one row and are inserted in a bottom portion of the needle seat 31. Acupuncture needles commercially available in the market can be used as the needles 32.

The temperature monitor 4 is connected to the needle assembly 3. In this embodiment, the temperature monitor 4 is a thermocouple, is connected to one of the needles 32 for detecting a temperature change of the same, and is able to transmit a signal in response to the temperature change.

The high frequency induction heating circuit unit 2 has two induction coils 200 capable of producing an electromagnetic field to induce currents in the ferrous needles 32 and to thereby heat the ferrous needles 32.

Preferably, the system further includes a heat insulation pad 5 disposed near the needle assembly 3 for isolating heat from the needle assembly 3. The heat insulation pad 5 is made of a flexible heat insulation material having low thermal conductivity.

When the electromagnetic thermotherapeutic system is used for curing a swollen portion of the organ 101, such as a swollen portion of a spleen, the following procedures are performed. A laparotomy is conducted such that the organ 101 is accessible. The needle seat 31 is bent and deformed into a shape that is conformable to a shape of the swollen portion of the organ 101. The needles 32 are inserted into the swollen portion of the organ 101 by virtue of an aseptic method such that the temperature monitor 4 is disposed adjacent to the organ 101. It should be noted that the temperature monitor 4 could be inserted into the organ 101 together with the needles 32. The temperature monitor 4 is electrically coupled to the high frequency induction heating circuit unit 2. A signal generated from the temperature monitor 4 can be transmitted to the high frequency induction heating circuit unit 2 so that the electromagnetic field generated by the high frequency induction heating circuit unit 2 can be controlled. Thus, the temperature of the needles 32 can be controlled. The heat insulation pad 5 is disposed between the organ 101 and other tissues 102 and organs (not shown), thereby isolating the heat from the needle assembly 3 and preventing damage to other tissues and organs.

After installation of the needle assembly 3, the temperature monitor 4, and the heat insulation pad 5, a patient's body 100 that has the organ 101 is disposed between the two induction coils 200. When the high frequency induction heating circuit unit 2 is energized, the high-frequency electromagnetic field produced by the induction coils 200 induces currents in the needles 32, thereby generating heat in the needles 32. The temperature monitor 4 detects the temperature of the needles 32 and transmits a signal to the high frequency induction heating circuit unit 2 so that the temperature of the needles 32 is maintained within a desired range. The swollen portion of the organ 101 is heated and destroyed through the needles 32. Via the color change of the needle seat 31, the user is able to know if the needles 32 are overheated. After the organ 101 is treated for a desired time, the high frequency induction heating circuit unit 2 is turned off, and the needle assembly 3, the temperature monitor 4, and the heat insulation pad 5 are removed.

When the electromagnetic thermotherapeutic system is applied to surgical resection for the organ 101 (e.g., surgical removal of a part of a liver), the following procedures are conducted. The needle seat 31 is bent and deformed into a shape conformable to a shape of an edge that belongs to a target part of the organ 101, which is required to be resected. The needles 32 are inserted into the organ 101 along the edge of the target part of the organ 101. The temperature monitor 4 is coupled to the high frequency induction heating circuit unit 2. The heat insulation pad 5 is disposed between the organ 101, and other tissues 102 and organs (not shown). The needles 32 are heated by the high frequency induction heating circuit unit 2 and are maintained at a desired temperature for a desired time. Consequently, tissues of the edge belonging to the target part of the organ 101 are cauterized and destroyed. Meanwhile, blood vessels of the edge belonging to the target part of the organ 101 are cauterized and closed off, thereby lowering the possibility of hemorrhage during the surgical resection and facilitating the surgical resection. There may even be no bleeding during the surgical resection when the system is used.

When the needles 32 are heated to cauterize and destroy the target biological tissue, other tissues adjacent to the target biological tissue are not easily damaged, since the heated needles 32 are only able to cauterize and destroy regions into which the needles 32 are inserted. In vivo experiments, such as a treatment of an animal swollen spleen and a surgical resection for an animal liver, were performed to test the system. The results show that the animal spleen treated using the system functions normally, and the animal liver treated using the system recovers well and has no abscess.

Some advantages of the electromagnetic thermotherapeutic system of this invention are as follows:

1. By the flexible and bendable structure of the needle seat 31, the user is capable of adjusting the way to insert the needles 32 into the biological tissue. Even though shapes of tissues vary, the needle assembly 3 is still suitable for the tissues having various shapes.

2. Since hemorrhage can be prevented through the needles 32, safety of a surgical operation employing the system can be enhanced.

3. Due to the signal communication between the temperature monitor 4 and the high frequency induction heating circuit unit 2, the temperature of the needles 32 is automatically controlled. Furthermore, the user is able to identify the temperature change of the needles 32 by observing the color change of the needle seat 31. Therefore, the system is safe for patients.

4. Since the structure of the needle assembly 3 is simple, a production cost of the same is much lower than a production cost of a heating needle used for radiofrequency ablation. A cost of a treatment utilizing the system is low as well, and the treatment can be widely used.

While the present invention has been described in connection with what is considered the most practical and preferred embodiments, it is understood that this invention is not limited to the disclosed embodiments but is intended to cover various arrangements included within the spirit and scope of the broadest interpretation and equivalent arrangements.

What is claimed is:

1. An electromagnetic thermotherapeutic apparatus that can be used to treat a biological tissue and that can be used in combination with a high frequency induction heating circuit unit, said electromagnetic thermotherapeutic apparatus comprising:

a needle assembly adapted to be inserted through the biological tissue, with the needle assembly including a flexible and bendable needle seat and a plurality of ferrous needles that can be induction heated by the high frequency induction heating circuit unit, with said plurality of ferrous needles attached to said needle seat and having needle tips extending in a direction away from said needle seat;
a temperature monitor connected to said needle assembly; and
a heat insulation pad separately formed from and disposed near said needle assembly, with the plurality of ferrous needles located intermediate the heat insulation pad and the needle seat for isolating heat from said plurality of ferrous needles of said needle assembly, with the heat insulation pad adapted to be located between the biological tissue through which the needle assembly is adapted to be inserted and another biological tissue to isolate the other biological tissue from the heat from said plurality of ferrous needles of said needle assembly.

2. The electromagnetic thermotherapeutic apparatus as claimed in claim 1, wherein said plurality of ferrous needles are disposed in one row, and wherein said needle seat is formed as a strip.

3. The electromagnetic thermotherapeutic apparatus as claimed in claim 1, wherein said needle seat includes a thermochromic material that can change in color in response to a temperature change of said plurality of ferrous needles.

4. The electromagnetic thermotherapeutic apparatus as claimed in claim 3, wherein said needle seat is made from a combination containing the thermochromic material and a flexible polymeric molding material.

5. The electromagnetic thermotherapeutic apparatus as claimed in claim 4, wherein the flexible polymeric molding material includes a material selected from the group consisting of silicone, rubber, and polydimethylsiloxane.

6. An electromagnetic thermotherapeutic system adapted to treat a biological tissue, said electromagnetic thermotherapeutic system comprising:
a needle assembly adapted to be inserted through the biological tissue, with the needle assembly including a flexible and bendable needle seat and a plurality of ferrous needles attached to said needle seat and having needle tips extending in a direction away from said needle seat;
a high frequency induction heating circuit unit having an induction coil producing an electromagnetic field to induce currents in said plurality of ferrous needles and to thereby heat said plurality of ferrous needles;
a temperature monitor connected to said needle assembly; and
a heat insulation pad separately formed from and disposed near said needle assembly, with the plurality of ferrous needles located intermediate the heat insulation pad and the needle seat for isolating heat from said plurality of ferrous needles of said needle assembly, with the heat insulation pad adapted to be located between the biological tissue through which the needle assembly is adapted to be inserted and another biological tissue to isolate the other biological tissue from the heat from said plurality of ferrous needles of said needle assembly.

7. The electromagnetic thermotherapeutic system as claimed in claim 6, wherein said plurality of ferrous needles are disposed in an array.

8. The electromagnetic thermotherapeutic system as claimed in claim 6, wherein said needle seat includes a thermochromic material that can change in color in response to a temperature change of said plurality of ferrous needles.

9. The electromagnetic thermotherapeutic system as claimed in claim 8, wherein said needle seat is made from a combination containing the thermochromic material and a flexible polymeric molding material.

10. The electromagnetic thermotherapeutic system as claimed in claim 9, wherein the flexible polymeric molding material includes a material selected from the group consisting of silicone, rubber, and polydimethylsiloxane.

\* \* \* \* \*